US006799991B2

(12) United States Patent
Williams et al.

(10) Patent No.: US 6,799,991 B2
(45) Date of Patent: Oct. 5, 2004

(54) MEDICAL LEAD CONNECTOR

(75) Inventors: Terrell M. Williams, Brooklyn Park, MN (US); John L. Sommer, Coon Rapids, MN (US)

(73) Assignee: Medtronic, Inc., Minneapolis, MN (US)

( * ) Notice: Subject to any disclaimer, the term of this patent is extended or adjusted under 35 U.S.C. 154(b) by 105 days.

(21) Appl. No.: 09/947,795

(22) Filed: Sep. 5, 2001

(65) Prior Publication Data

US 2003/0045912 A1 Mar. 6, 2003

(51) Int. Cl.[7] .................................................. H01R 11/18
(52) U.S. Cl. ........................................ 439/482; 439/462
(58) Field of Search ................................. 439/462, 411, 439/431, 434, 263, 727, 728, 806, 909

(56) References Cited

U.S. PATENT DOCUMENTS 203,931 A * 5/1878 Nickerson .................... 279/42
1,342,819 A 6/1920 Lake
3,040,292 A 6/1962 Bernard
3,509,517 A * 4/1970 Gutshall ..................... 439/411
3,824,556 A * 7/1974 Berkovits et al. ........... 439/727
3,842,394 A * 10/1974 Bolduc ....................... 439/261
4,195,895 A * 4/1980 Ziegler ........................ 439/99
4,540,236 A * 9/1985 Peers-Trevarton .......... 439/159
4,784,141 A * 11/1988 Peers-Trevarton ........... 607/37
5,007,864 A 4/1991 Stutz, Jr.
5,069,209 A * 12/1991 Posin .......................... 607/37
5,231,996 A 8/1993 Bardy et al.
5,489,225 A * 2/1996 Julian ......................... 439/837
5,730,628 A * 3/1998 Hawkins ..................... 439/843
5,904,587 A * 5/1999 Osypka et al. .............. 439/263
6,428,336 B1 * 8/2002 Akerfeldt .................... 439/263

* cited by examiner

*Primary Examiner*—Chandrika Prasad
(74) *Attorney, Agent, or Firm*—Girma Wolde-Michael; Michael C. Soldner

(57) ABSTRACT

An electrical connector has a compressible portion that expands to accept an inserted lead and then contracts around the lead to provide both an electrical and a spring-like mechanical connection to the lead. The connector may have a fluted pin that collapses around the lead body when a set screw of the connector port is tightened. Alternatively, a middle segment of a pin may have indentations or slots that collapse around an inserted lead body. The connector can be attached to the lead body after the lead body is implanted in the body of the patient. In lead systems in which the lead body is implanted using a guide catheter, attaching the connector to the lead body after implantation makes removal of the guide catheter much less difficult.

12 Claims, 4 Drawing Sheets

58 50 52 52 54 64 56 58 60 62 56 64 58

MEDICAL LEAD CONNECTOR

FIELD

The invention relates to implantable medical devices and, more particularly, to electrical leads for use with such devices.

BACKGROUND

Implantable medical devices (IMDs), such as implantable cardioverter/defibrillators (ICDs) and pacemaker/cardioverter/defibrillators (PCDs), can detect and administer therapy for a variety of conditions. These conditions include ventricular fibrillation (VF), atrial fibrillation (AF), tachycardia, and bradycardia.

Various types of transvenous pacing and cardioversion/defibrillation leads have been developed for use with IMDs. These leads are typically flexible to facilitate insertion and placement into the body of the patient, and are usually constructed with an outer polymeric sheath encasing a coiled wire conductor. The coiled wire conductor is typically attached at a distal end to a shank portion of a tip electrode. A proximal end of the coiled wire conductor is coupled to a lead connector end assembly.

Different manufacturers often produce implantable cardiac leads with lead connector end assemblies that match connector block terminals of IMDs from a common manufacturer. More recently, a number of manufacturers have adopted a single dimensional pacemaker connector standard known as the low-profile connector "IS-1" standard (ISO 5841-3:1992(E)) for bipolar in-line and unipolar lead connector end assemblies. Compatibility with the IS-1 standard ensures that leads made by one manufacturer can be interchangeably used in connection with an IMD made by a different manufacturer.

In some conventional lead systems, a lead body is implanted through a guide catheter, which is then pulled off the lead body after implantation. Typically, the electrical connector attached to the end of the lead body has a larger diameter than the lead body. As a result, in such lead systems, pulling the guide catheter off the lead body can be difficult. Moreover, some connectors do not implement the low- profile design of the IS-1 standard, making post-implantation removal of the guide catheter even more difficult. In lead systems implementing such high-profile connectors, the guide catheter used must have a larger diameter, making lead placement in some places, such as the coronary sinus, difficult.

SUMMARY

The invention is generally directed to electrical connectors that can be attached to an implanted lead body. More particularly, various embodiments of the invention provide electrical connectors that have a compressible portion that expands to accept an inserted lead and then contracts around the lead to provide both an electrical and a springlike mechanical connection to the lead. In one embodiment, the connector has a fluted pin that collapses around the lead body when a set screw of the connector port is tightened. In another embodiment, a middle segment of a pin has indentations or slots that collapse around an inserted lead body. Both embodiments are compatible with the IS-1 standard for pacemaker leads.

The invention provides a number of advantages. For example, the electrical connector can be attached to the lead body after the lead body is implanted in the body of a patient. In lead systems in which the lead body is implanted using a guide catheter, attaching the connector to the lead body after implantation allows removal of the guide catheter before the connector is attached. Because the guide catheter does not have to overcome mechanical resistance imparted by the larger diameter of the connector compared to the lead body, removal of the guide catheter is facilitated.

One embodiment of the invention is directed to an electrical connector that includes a first portion that defines a channel for receipt of a medical lead. An electrically conductive collapsible portion is operatively coupled to the first portion and is arranged to collapse around a portion of the medical lead upon receipt of the medical lead in the channel.

In a specific embodiment, the collapsible portion comprises a proximal portion of the electrical connector that has longitudinal slots that cause the proximal portion to collapse around the portion of the medical lead when a set screw of a connector port is tightened. When tightened, the set screw applies a force to the proximal portion that causes the proximal portion of the connector to collapse around the lead.

In another specific embodiment, the collapsible portion comprises a middle portion of the electrical connector that is disposed between the first portion of the connector and a proximal portion of the electrical connector. The middle portion has a slot arranged to cause the middle portion to collapse around the portion of the medical lead. These connectors may be implemented as part of a lead system.

Another embodiment of the invention is directed to a method of attaching an electrical connector to a medical lead. The medical lead is implanted in the body of the patient. A portion of the medical lead is threaded through a distal portion of an electrical connector. Next, an electrically conductive collapsible portion of the electrical connector is caused to collapse around the portion of the medical Icad, for example, by tightening a set screw of a connector port to apply a force to the collapsible portion.

The above summary of the invention is not intended to describe every embodiment of the invention. The details of one or more embodiments of the invention are set forth in the accompanying drawings and the description below. Other features, objects, and advantages of the invention will be apparent from the description and drawings, and from the claims.

DETAILED DESCRIPTION

Figure 1:
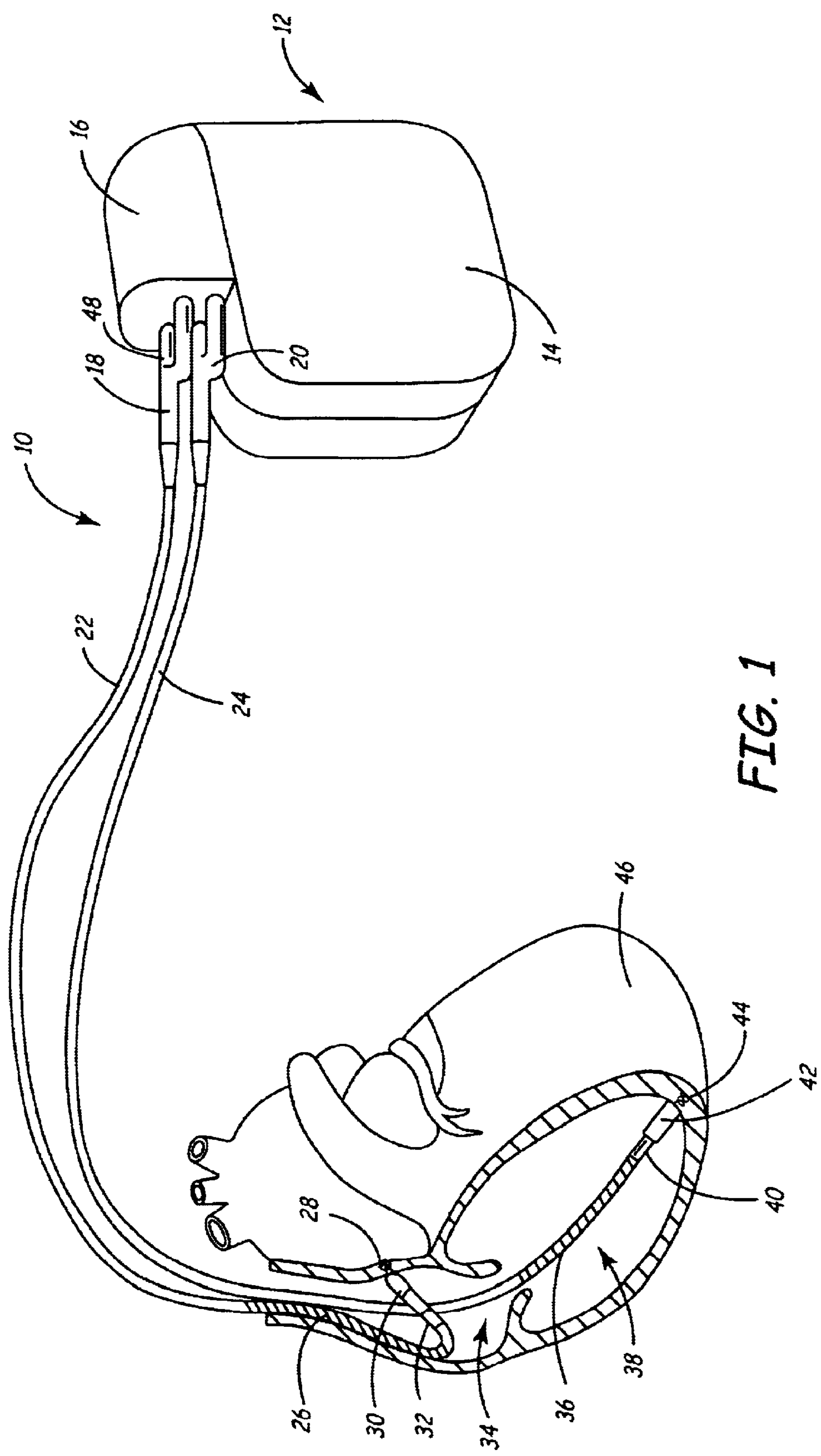
FIG. 1 is a diagram illustrating an implantable medical device system.

FIG. 1 illustrates an implantable medical device (IMD) system 10 in which the present invention may be practiced. IMD system 10 is shown in association with a human heart 46. As shown in FIG. 1, IMD system 10 includes a pacernaker/cardioverter/defibrillators (PCD) 12 having a housing 14 and a connector block 16. IMD system 10 may be implemented using any of a number of medical devices, including, but not limited to, PCD 12 or an implantable cardiac defibrillator (ICD). Other techniques or therapies responsive to EGM signals, such as therapies that administer drugs in response to atrial arrhythmia, also may implement various embodiments of the invention.

Optionally, insulation of the outward facing portion of housing 14 of PCD 12 may be provided using a plastic coating, such as parylene or silicone rubber, as is employed in some unipolar cardiac pacemakers. However, the outward facing portion may instead be left uninsulated, or some other division between insulated and uninsulated portions may be employed. The uninsulated portion of the housing 14 optionally serves as a subcutaneous defibrillation electrode, used to defibrillate either the atria or ventricles.

IMD system 10 comprises a ventricular lead, which includes an elongated insulated lead body 24, carrying three concentric coiled conductors separated from one another by tubular insulative sheaths. The distal end of the ventricular lead is deployed in right ventricle 38. Located adjacent the distal end of the ventricular lead arc a ring electrode 40, an extendable helix electrode 44, mounted retractably within an insulative electrode head 42, and an elongated (approximately 5 cm) defibrillation coil electrode 36. Defibrillation electrode 36 may be fabricated from many materials, such as platinum or platinum alloy. Each of the electrodes is coupled to one of the coiled conductors within lead body 24.

Electrodes 40 and 44 are employed for cardiac pacing and for sensing ventricular depolarizations. Accordingly, electrodes 40 and 44 serve as sensors for a V-EGM. At the proximal end of the ventricular lead is a bifurcated connector 20 that carries three electrical connectors, each coupled to one of the coiled conductors.

The atrial/superior vena cava (SVC) lead includes an elongated insulated lead body 22, carrying three concentric coiled conductors, separated from one another by tubular insulative sheaths, corresponding to the structure of the ventricular lead. The distal end of the atrial/SVC lead is deployed in right atrium 34. Located adjacent the distal end of the atrial/SVC lead are a ring electrode 32 and an extendable helix electrode 28, mounted retractably within an insulative electrode head 30. Each of the electrodes is coupled to one of the coiled conductors within lead body 22. Electrodes 28 and 32 are employed for atrial pacing and for sensing atrial depolarizations. Accordingly, electrodes 28 and 32 serve as sensors for an A-EGM.

An elongated coil electrode 26 is provided proximal to electrode 32 and coupled to the third conductor within lead body 22. Electrode 26 is preferably at least 10 cm long and is configured to extend from the SVC toward the tricuspid valve. At the proximal end of the lead is a bifurcated connector 18 that carries three electrical connectors, each coupled to one of the coiled conductors.

Implantable PCD 12 is shown in combination with the leads, with lead connector assemblies 18 and 20 inserted into low-profile IS-1 type connector ports 48 on connector block 16. Although an IS-1 type connector may employ the current invention, it will be understood that the invention may also be utilized with any other type of standard or non-standard connector. For example, the invention is particularly useful when larger-profile connectors are utilized, since these connectors make guide catheter removal more difficult following lead placement during an implant procedure.

According to various embodiments of the invention, one or more of lead connector assemblies 18 and 20 may have a compressible portion that expands to accept an inserted lead and then contracts around the lead to provide both an electrical and a spring-like mechanical connection to the lead. In one embodiment, the connector has a fluted pin that collapses around the lead body when a set screw of the connector port is tightened. In another embodiment, a middle segment of a pin has indentations or slots that collapse around an inserted lead body. Both embodiments are compatible with the IS-1 standard for pacemaker leads.

The invention provides a number of advantages. For example, the electrical connector can be attached to the lead body after the lead body is implanted in the body of the patient In lead systems in which the lead body is implanted using a guide catheter, attaching the connector to the lead body after implantation allows removal of the guide catheter before the connector is attached. Because the guide catheter does not have to overcome mechanical resistance imparted by the larger diameter of the connector compared to the lead body, removal of the guide catheter is facilitated.

Figure 2:
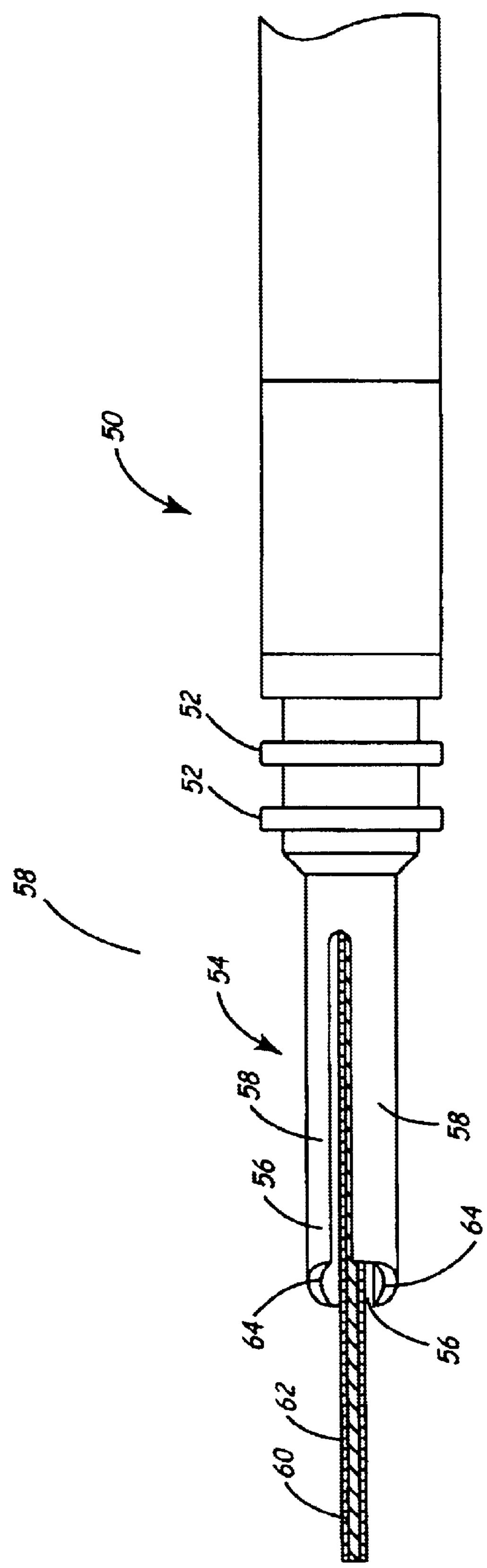
FIG. 2 is a sectional view of an electrical connector for use with the implantable medical device system of FIG. 1, according to an embodiment of the present invention.

FIG. 2 is a side view of an example electrical connector assembly 50 that may be attached to the end of lead body 22 or 24 of FIG. 1. Electrical connector assembly 50 can be used with a variety of leads, including leads compliant with the IS-1 standard for pacemaker leads. As shown in FIG. 2, connector assembly 50 includes sealing rings 52 and an electrically conductive connector pin 54 having a number of longitudinal slots 56 cut along the perimeter of the proximal end of pin 54 so as to form a number of flanges 58. Sealing rings 52 protect connector pin 54 and PCD 12 against ingress of external contaminants.

A lead body includes an elongated lead conductor 60 formed of coiled wire covered with an insulator 62, which may be fabricated of silicone rubber, polyurethane, or other suitable plastic. The lead body may be implanted within a vein of the patient with an electrode at its distal end affixed to tissue in the right ventricle of the patient A guide catheter, guide wire, and/or any other lead delivery device may be used to facilitate placement of the lead body. These delivery devices are removed after the lead body is implanted.

After the guide catheter is removed, connector assembly 50 is attached at the proximal end of the lead body by threading lead conductor 60 through connector assembly 50. The portion of lead conductor 60 that protrudes from the tip of connector pin 54 may then be cut off to the desired length. As an alternative, pin 54 may be manufactured with longitudinal slots 56 extending across less than the entire length of the proximal end of pin 54. With this construction, the tip of pin 54 is closed such that lead conductor 60 does not protrude from pin 54.

After lead conductor 60 is threaded through connector body 50, pin 54 is inserted into IS-1 connector port 48 on the pacemaker. The IS-1 connector port has a set screw 65 that, when tightened, contacts and applies a force to one of the flanges 58, causing it to deflect toward lead conductor 60. As a result, pin 54 collapses around and grips lead conductor 60. Flange 58 has a sharp edge 64 that breaches insulator 62 when flange 58 is deflected by tightening the set screw 65, making contact with lead conductor 60. By causing pin 54 to grip lead conductor 60 and to breach insulator 62, t set screw 65 establishes both a mechanical connection and an electrical connection between the connector port, pin 54, and lead conductor 60.

Advantageously, attaching connector assembly 50 to the lead body after implanting the lead body facilitates removal of the guide catheter, as the guide catheter does not need to overcome the mechanical resistance that would otherwise be presented by the larger diameter of connector assembly 50 compared to lead conductor 60.

Figure 3:
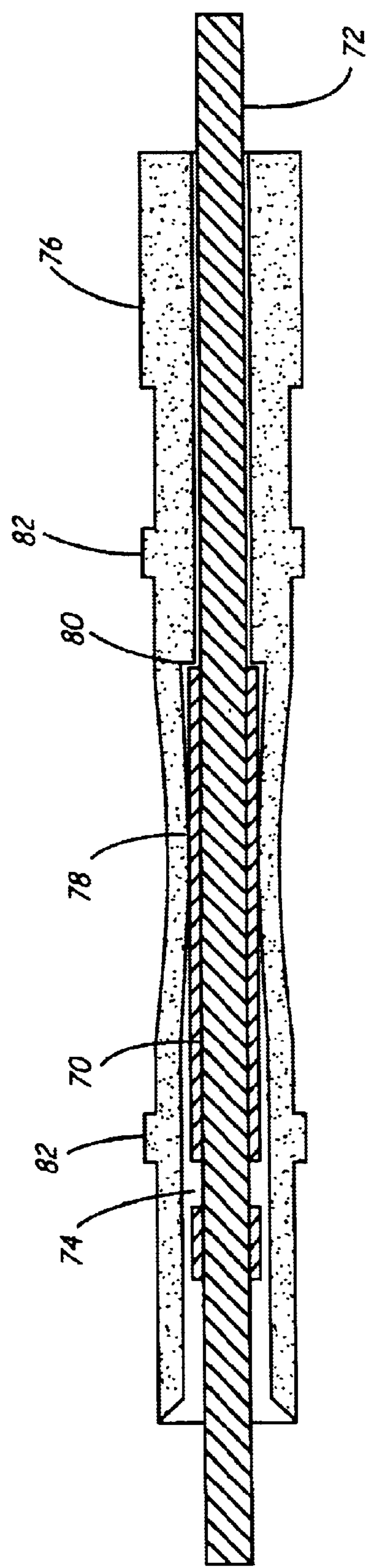
FIG. 3 is a sectional view of another electrical connector for use with the implantable medical device system of FIG. 1, according to another embodiment of the present invention.

According to another embodiment of the present invention illustrated in FIG. 3, an electrically conductive sleeve 70 is crimped on a lead body 72 to make electrical contact with lead body 72 and is secured to lead body 72 with adhesive. While not required, optional apertures 74 in sleeve 70 may provide visual confirmation that adhesive has been used to secure lead body 72. Lead body 72 with crimped sleeve 70 is then pulled through an electrically conductive connector body 76 having a deflectable section 78. Deflectable section 78 may be formed, for example, by forming slots on connector body 76 using electron displacement machining (EDM) or another suitable technique. The slots are deflected to provide an interference fit with sleeve 70. The slots impart some flexibility to deflectable section 78. In a nondeflected state, deflectable section 78 has an inner diameter smaller than the outer diameter of sleeve 70. As a result, when sleeve 70 is pulled through connector body 76, deflectable section 78 expands to accept sleeve 70. Deflectable section 78 thereby exerts a spring force on sleeve 70 to secure sleeve 70 in place. The spring force establishes mechanical and electrical contact between connector body 76, sleeve 70, and lead body 72. In addition, connector body 76 may include a stop 80 to prevent sleeve 70 from being pulled beyond stop 80.

Connector body 76 may be molded inside a tube (not shown) and secured with silicone rubber. To isolate the portion of sleeve 70 exposed by the slots formed on deflectable section 78, connector body 76 includes a number of sealing rings 82. Sealing rings 82 form a seal with the tube to prevent ingress of the silicone rubber into deflectable section 78, thereby preventing contact between the silicone rubber with sleeve 70.

Figure 4:
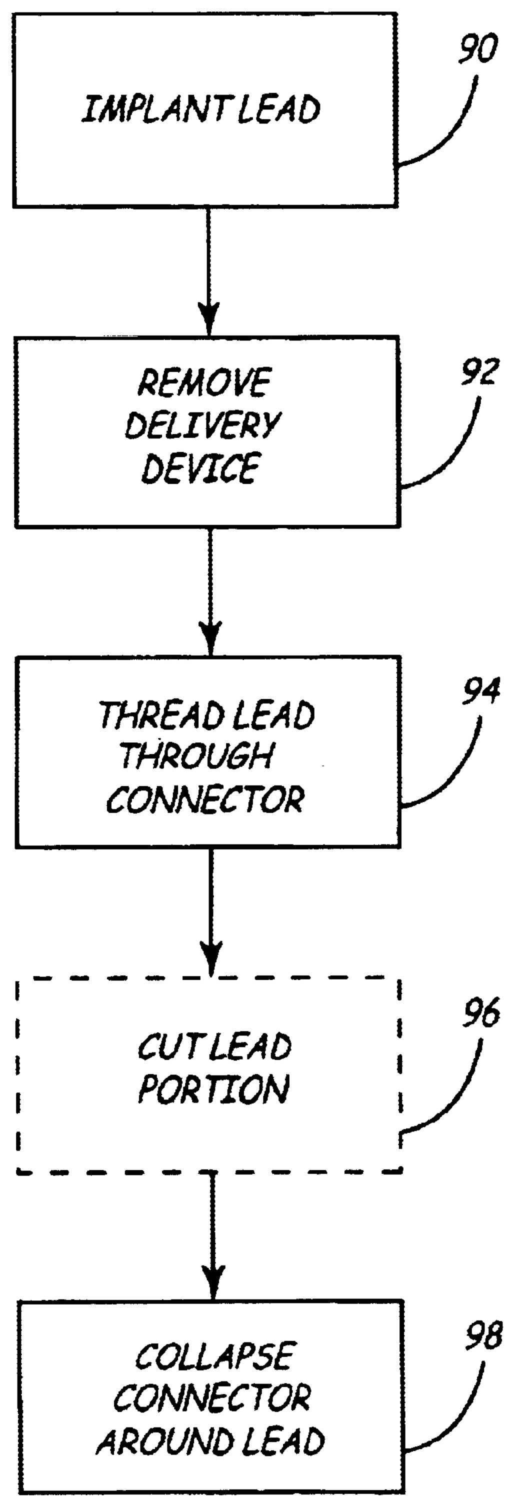
FIG. 4 is a flow diagram depicting an example process for attaching an electrical connector to a medical lead, according to still another embodiment of the invention.

FIG. 4 is a flow diagram depicting an example process for attaching an electrical connector to a medical lead, according to still another embodiment of the invention. First, the medical lead is implanted in the body of the patient (90). Implanting the lead typically involves attaching a distal end of the lead to cardiac tissue and using a guide catheter, introducer sheath, or other delivery device to facilitate proper placement of the lead. The delivery device is then withdrawn from the body of the patient (92) before attaching the connector. After the lead is placed, a proximal portion of the lead is threaded through a distal portion of an electrical connector (94), such as the connector shown in FIG. 2 or the connector shown in FIG. 3. Advantageously, attaching the connector after withdrawing the delivery device from the body facilitates removal of the delivery device. In addition, while not required, a portion of the lead extending proximal to the connector is optionally cut off (96) after the connector is positioned. Accordingly, the lead length can be tailored to the physiology of the patient To establish mechanical and electrical contact between the lead and the connector, an electrically conductive collapsible portion of the electrical connector is caused to collapse around the portion of the medical lead (98). As described above in connection with FIG. 2, this may be achieved by tightening a set screw, thereby applying a force to the connector that causes the connector to tighten around the lead. Alternatively, if the connector shown in FIG. 3 is used, the connector may be collapsed around the lead by removing a silicone introducer and thereby creating a spring force that establishes mechanical and electrical contact.

As described above, the invention may provide certain advantages in the implantation process. For example, the connectors shown in FIGS. 2–3 may be attached to a lead body after the lead body is implanted in the patient As a result, a guide catheter used to promote proper placement of the lead body can be easily removed from the lead body without having to overcome mechanical resistance presented by a connector having a larger diameter than the lead body. Various embodiments of the invention have been described. These embodiments are illustrative of the practice of the invention. These and other embodiments are within the scope of the following claims.

What is claimed is:

1. An electrical connector configured for insertion in to an implantable medical device to electrically couple the implantable medical device and the electrical connector, the electrical connector comprising:

a first portion defining a channel to receive a medical lead; and an electrically conductive collapsible portion operatively coupled to the first portion and arranged to collapse around a portion of the medical lead upon receipt of the medical lead in the channel, wherein the collapsible portion comprises a proximal portion of the electrical connector, the proximal portion having a plurality of longitudinal slots that cause the proximal portion to collapse around the portion of the medical lead when a set screw of a connector port is tightened.

2. The electrical connector of claim 1, wherein the longitudinal slots extend across less than an entire length of the proximal portion.

3. The electrical connector of claim 1, wherein the longitudinal slots, define flanges in the proximal portion, the flanges including sharp edges to breach an insulative portion of the medical lead in conjunction with positioning of the set screw.

4. A lead system comprising:

a lead; and an electrical connector contoured to receive the lead and for insertion into an implantable medical device to electrically couple the implantable medical device to the lead, the electrical connector comprising a first portion defining a channel to receive the lead and an electrically conductive collapsible portion operatively coupled to the first portion and arranged to collapse around a portion of the lead upon receipt of the lead in the channel, wherein the collapsible portion comprises a proximal portion of the electrical connector, the proximal portion having a plurality of longitudinal slots that cause the proximal portion to collapse around the portion of the lead when a set screw of a connector port is tightened, thereby applying a force to the proximal portion.

5. The lead system of claim 4, wherein the longitudinal slots extend across less than an entire length of the proximal portion.

6. The lead system of claim 4, wherein the longitudinal slots define flanges in the proximal portion, the flanges including sharp edges to breach an insulative portion of the lead when the set screw is tightened.

7. A lead system comprising:

a lead including an electrically conductive sleeve crimped on the lead; and an electrical connector configured to receive the lead and for insertion into an implantable medical device to electrically couple the implantable medical device to the lead, the connector including a connector body defining a channel to receive a medical lead, a deflectable section to electrically couple to and exert a spring force on the lead when the lead is inserted through the channel, and a stop formed in the channel to abut the electrically conductive sleeve crimped on the lead and prevent the medical lead from being pulled beyond the stop.

8. A method of attaching an electrical connector configured for insertion into an implantable medical device to a medical lead, the method comprising:

implanting the medical lead;

threading a portion of the medical lead through a distal portion of the electrical connector;

causing an electrically conductive collapsible portion of the electrical connector to collapse around the portion of the medical lead; and causing the collapsible portion to collapse by tightening a set screw of a connector port to apply a force to the collapsible portion.

9. The method of claim 8, wherein the collapsible portion comprises a proximal portion of the electrical connector, the proximal portion having a plurality of longitudinal slots that cause the proximal portion to collapse around the portion of the medical lead upon application of the force by the set screw.

10. The method of claim 9, wherein the longitudinal slots extend across less-than an entire length of the proximal portion.

11. The method of claim 8, wherein the longitudinal slots define flanges in the proximal portion, the flanges including sharp edges to breach an insulative portion of the medical lead when the set screw is tightened.

12. A method of attaching an electrical connector configured for insertion into an implantable medical device to a medical lead, the method comprising:

implanting, the medical lead, the medical lead including an electrically conductive sleeve crimped on the lead;

threading a portion of the medical lead through a distal portion of the electrical connector, the electrical connector including a deflectable section to electrically couple to and exert a spring force on the lead when the lead is inserted through the channel and a stop formed in the channel; and pulling the lead through the electrical connector such that the electrically conductive sleeve abuts the stop.

* * * * *